United States Patent [19]

Harris

[11] 4,324,761
[45] Apr. 13, 1982

[54] HYDROGEN DETECTOR

[75] Inventor: Lawrence A. Harris, Schenectady, N.Y.

[73] Assignee: General Electric Company, Schenectady, N.Y.

[21] Appl. No.: 249,790

[22] Filed: Apr. 1, 1981

[51] Int. Cl.³ .................. G01N 27/40; G01N 27/12; G01N 31/06
[52] U.S. Cl. .................. 422/98; 324/71 SN; 338/34; 422/95
[58] Field of Search .................. 422/97, 96, 98, 94, 422/95; 23/232 E; 338/34; 324/71 SN

[56] References Cited

U.S. PATENT DOCUMENTS 3,479,257 11/1969 Shaver .................. 422/95
3,999,947 12/1976 Mihara .................. 422/95
4,058,368 11/1977 Svensson et al. .................. 23/254

OTHER PUBLICATIONS

Yamamoto et al., "Surface Science," vol. 92, (Feb. 11, 1980), pp. 400-406.

Primary Examiner—Ronald Serwin
Attorney, Agent, or Firm—Jane M. Binkowski; James C. Davis, Jr.; Joseph T. Cohen

[57] ABSTRACT

A hydrogen detector comprised of a substrate supporting an electrically conducting base metal film, an upper electrically conducting duffusion barrier metal film, a polycrystalline film of titanium dioxide sandwiched between the base and diffusion barrier films, said polycrystalline titanium dioxide film electrically insulating the base film from said diffusion barrier film, the base film being in electrical contact with the titanium dioxide film, an insulating layer electrically insulating said titanium dioxide film from said diffusion barrier film except for a predetermined surface portion thereof in electrical contact with said diffusion barrier film, said predetermined electrically contacting portion being at least sufficiently large to produce a measurable electrical conductance, an electrically conducting or non-conducting catalytic top film of metal able to dissociate hydrogen into its atomic form in electrical contact with said diffusion barrier film and at least substantially coextensive with said barrier film throughout said predetermined electrically contacting portion, said top film when it is electrically conducting or said diffusion barrier film and said base film being connected to an external circuit to measure conductance, the electrical conductance of said hydrogen detector varying with the concentration of hydrogen in the atmosphere surrounding it.

20 Claims, 4 Drawing Figures

HYDROGEN DETECTOR

This invention relates to a hydrogen detecting device with an electrical conductivity influenced strongly by the hydrogen content of the surrounding atmosphere.

The many industrial and possibly future domestic uses for hydrogen require simple sensitive means for detecting hydrogen leaks or for measuring hydrogen concentrations. Current research efforts on production of hydrogen by decomposition of water (by chlorophyll and other organometallic substrates) also demand simple and sensitive means for detecting minute quantities of hydrogen.

Thin film semiconductor hydrogen detectors have been described by several workers in the past. These detectors exhibited a marked increase in surface conductivity in the presence of hydrogen. Though extremely sensitive to hydrogen, the detectors also responded to other materials such as carbon dioxide, benzene, ethanol, and hydrazine, ammonia, and hydrogen sulfide as well as other materials. They also had to be operated at temperatures generally above 250° C.

The present invention provides a simple, reliable, hydrogen detector that does not respond strongly to other gases and that is operable at room temperature. In the present detector excess carriers are introduced by absorption of hydrogen, but electrical conductance is measured through the films instead of along the surface of a film. Since this device depends on the presence of donors in the bulk instead of adsorbed on the surface, it is substantially more selective toward hydrgoen.

In Ser. No. 249,791 for "Hydrogen Detector" filed of even date herewith in the name of L. A. Harris, assigned to the assignee hereof and incorporated herein by reference, there is disclosed a hydrogen detector comprised of a substrate supporting an electrically conducting base metal film, an electrically conducting top film of metal able to dissociate hydrogen into atomic form, a polycrystalline film of titanium dioxide ($TiO_2$) sandwiched between the base and top films, said polycrystalline titanium dioxide film electrically insulating the base film from said top film, the base film being in electrical contact with the titanium dioxide film, an insulating layer electrically insulating said titanium dioxide film from said top film except for a predetermined surface portion thereof in electrical contact with said top film, said predetermined electrically contacting portion being at least sufficiently large to produce a measurable electrical conductance, said top and base films being connected to an external circuit to measure conductance, the electrical conductance of said hydrogen detector varying with the concentration of hydrogen in the atmosphere surrounding it.

The hydrogen detector of Ser. No. 249,791 is an effective alarm device for small concentrations of $H_2$ in air, and can give a quantitative response for concentrations up to about 0.3%. Above about 0.5% the current through the detector is limited by lead resistance and is no longer quantitatively related to hydrogen concentration. For some applications it may be desirable to measure greater concentrations. The present invention is directed to a detector useful for that purpose. It has been found that if greater concentrations are to be measured, the sensitivity can be reduced by interposing a thin metallic diffusion barrier between the active $TiO_2$ layer and the catalytic top film of Pt or Pd.

In the present invention, means are provided for adjusting the sensitivity of a solid state titanium dioxide hydrogen sensor so that it can measure hydrogen concentrations in a desired range.

It is believed that the sensitivity and speed of response are determined by the kinetic balance among a number of processes. These include primarily, the rate of hydrogen dissociation to atoms on the catalytic film, the rate at which these atoms diffuse into or out of the $TiO_2$ layer and the rate of water formation by reaction of hydrogen with ambient oxygen on the catalytic film.

By interposing a thin metallic film between the $TiO_2$ and the catalytic layer, the rate of H diffusion into the $TiO_2$ (which ultimately determines the current) will be slowed relative to the rate of water formation at the surface. The hydrogen concentration necessary to produce a given current will thus be increased, i.e., the sensitivity will be reduced.

Briefly stated, the present hydrogen detector is comprised of a substrate supporting an electrically conducting base metal film, an upper electrically conducting diffusion barrier metal film, a polycrystalline film of titanium dioxide sandwiched between the base and diffusion barrier films, said polycrystalline titanium dioxide film electrically insulating the base film from said diffusion barrier film, the base film being in electrical contact with the titanium dioxide film, an insulating layer electrically insulating said titanium dioxide film from said diffusion barrier film except for a predetermined surface portion thereof in electrical contact with said diffusion barrier film, said predetermined electrically contacting portion being at least sufficiently large to produce a measurable electrical conductance, an electrically conducting or non-conducting catalytic top film of metal able to dissociate hydrogen into its atomic form in electrical contact with said diffusion barrier film and at least substantially coextensive with said barrier film throughout said predetermined electrically contacting portion, said top film when it is electrically conducting or said diffusion barrier film and said base film being electrically connected to an external circuit to measure conductance, the electrical conductance of said hydrogen detector varying with the concentration of hydrogen in the atmosphere surrounding it.

A small voltage is applied between the base metal and the top catalytic metal films and the current measured. The current increases markedly in the presence of hydrogen.

BRIEF DESCRIPTION OF THE DRAWINGS

Those skilled in the art will gain a further and better understanding of the present invention from the detailed description set forth below, considered in conjunction with the figures accompanying and forming a part of the specification, in which:

A plan view of one form of the present detector 3 is shown in FIG. 1. FIG. 2 shows a cross sectional view of the detector of FIG. 1 taken along line 2—2. Specifically, in detector 3 electrically insulating or non-insulating substrate 9 supports a base film of metal 7. A polycrystalline film of $TiO_2$ 6 is sandwiched between base film 7 and diffusion barrier metal film 11 and electrically insulates base film 7 from diffusion barrier metal film 11. Insulating layer 5 electrically insulates $TiO_2$ film 6 from diffusion barrier film 11 except for a predetermined effective portion 10 where $TiO_2$ film 6 is in electrical contact with diffusion barrier film 11. Top metal film 4 is in electrical contact with the diffusion barrier metal film 11. Also, top metal film 4 is at least substantially coextensive with barrier film 11 throughout the predetermined effective portion 10. Electrical contact 8 on top film 4 when film 4 is electrically conducting and an electrical contact (not shown) on base film 7 are used to electrically connect top film 4 and base film 7 to an external circuit for measuring conductivity.

Figure 1:
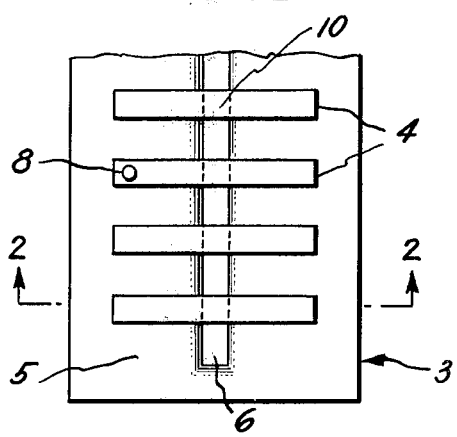
FIG. 1 is a plan view of one form of a series of the present detectors.

Alternatively, an electrical contact can be placed on diffusion barrier film 11 and used along with the electrical contact on base film 7 to electrically connect diffusion barrier film 11 and base film 7 to an external circuit for measuring conductance.

The substrate preferably is electrically insulating. For examples, it can be made of a material such as glass, quartz, a ceramic such as alumina or a plastic such as polystyrene. However, the metal used as the base metal film could be made thicker so that it also could be used as a supporting substrate. Its thickness affects primarily the recovery time, i.e. the period of time required to restore the detector to its original state after hydrogen is removed from its surrounding atmosphere.

The substate should have a surface suitable for supporting the present films, and preferably, such surface is planar and smooth. To promote adherence of the film, the substrate should be cleaned in a conventional manner before being used. For best results, it should be degreased, for example, by dipping in acetone. Also, preferably, the supporting surface of the substrate is sputter etched.

The base metal film 6 must be at least sufficiently thick to be electrically conducting. Generally, the base metal film ranges in thickness from about 100 Å to about 1000 Å, and preferably, from about 200 Å to about 500 Å. Films thicker than about 1000 Å provide no significant advantage and may slow recovery time. The base film of metal is preferably selected from the group consisting of titanium, gold, silver, nickel, indium, tin, copper and alloys thereof. Most preferably, it is titanium.

Top film 4 can be electrically conducting or non-conducting, and preferably, it is selected from the group consisting of platinum, palladium and alloys thereof.

In the embodiment of the present detector where top film 4 is electrically conducting, it must be at least sufficiently thick to be electrically conducting and film 4 or diffusion barrier 11 can be used for electrical contact. When film 4 is electrically conducting, its thickness generally ranges from about 100 Å to about 1000 Å, and preferably, from about 200 Å to about 500 Å. Film 4 should not be so thick as to slow the response time significantly.

In the embodiment where top film 4 is electrically non-conducting, it need only have a thickness at least sufficient to provide the catalytic properties of the metal, i.e. the ability to dissociate hydrogen into its atomic form, and such thickness would be less than about 100 Å. In this embodiment, diffusion barrier film 11 is used for electrical contact.

The upper diffusion barrier film 11 must be at least sufficiently thick to be electrically conducting. Its specific thickness depends largely on the concentration of hydrogen for which a qualitative or quantitative response is desired. Generally, with increasing concentration of hydrogen to be measured, the thickness of the diffusion barrier film is increased correspondingly. For most applications, the diffusion barrier film ranges in thickness from about 100 Å to about 1000 Å, and preferably, from about 200 Å to about 500 Å. The diffusion barrier film is a metal preferably selected from the group consisting of gold, silver, nickel, indium, tin, copper and alloys thereof. It has been found that titanium is not operable as a diffusion barrier film.

The polycrystalline film of titanium dioxide 7 must be at least sufficiently thick and integral to be electrically insulating but not so thick as to slow the response time significantly. Generally, its thickness ranges from about 500 Å to about 5000 Å, but preferably, from about 1000 Å to about 3000 Å.

A number of conventional techniques can be used to deposit or form the base metal film, the titanium dioxide film, the diffusion barrier film and the top metal film. Representative of these techniques are sputtering and vapor deposition.

The insulating layer 5 between the diffusion barrier metal film 11 and the $TiO_2$ film 6 need only to be sufficiently thick to be electrically insulating. It can be formed of any insulating material which has no significant deteriorating effect on the hydrogen detector. Representative of the materials useful for forming the insulating layer are lacquer or other polymer film-forming material and silicon monoxide. The insulating layer can be deposited and formed in conventional manner depending on the material itself. For example, it can be brushed on and, if necessary, treated with thermosetting means, or in the case of materials such as silicon monoxide, by vapor deposition.

The insulating layer 5 electrically insulates the $TiO_2$ film 6 from diffusion barrier metal film 11 except for a predetermined effective portion 10 where $TiO_2$ film 6 is in electrical contact with diffusion barrier metal film 11. The atoms produced by dissociation of hydrogen in top metal film 4 travel through this predetermined electrically contacting portion 10 into $TiO_2$ film 6. Therefore, this electrically contacting portion 10 should be at least sufficiently large to be effective, i.e., it should be at least sufficiently large to produce a measurable electrical conductance. As the electrically contacting portion 10 is increased, electrical conductance of the detector is increased but the probability of a short circuit due to a defect in a film is also increased. Generally, this contacting portion 10 between $TiO_2$ film 6 and diffusion barrier metal film 11 ranges from about 2 square millimeters (mm) to about 8 square mm, and typically, it is about 5 square mm.

The dc voltage required for operation of the present detector are generally smaller than those available from batteries, so that appropriate series resistors, doubling as current sensing elements, would be needed if the detectors are battery-operated. Nevertheless, low- and moderate-frequency ac methods are also applicable so that a considerable variety of instrumentation circuitry can be devised.

The present detector is operable through a wide range of temperatures, and it is particularly useful from about room temperature up to about 300° C. The response rate, but not the sensitivity, is strongly increased by a moderate rise in temperature. Temperatures above about 300° C. might come dangerously close to effecting a permanent reduction of the $TiO_2$ to a highly conducting state.

The present detector can measure hydrogen quantitatively at concentrations in excess of about 0.25%.

Response rate depends largely on the amount of hydrogen present in the surrounding atmosphere and the thickness of the diffusion barrier film.

The preferred mode of operation is with a Pt film negative with respect to a base film of Ti. This polarity makes the detector virtually unresponsive to other gases at room temperature, and almost so even at higher temperatures.

The diffusion of hydrogen into and out of the detector appears to be quite reversible. Air or oxygen is generally needed to remove hydrogen from the detector once the source of $H_2$ is cut off.

Significant advantages of the present detector are its effectiveness as an alarm for hydrogen, particularly for nuclear reactors, and its ability to measure hydrogen in ranges of hydrogen concentrations that can be chosen by its design. It is operable at room temperature and requires simple circuitry that uses negligible power in the absence of hydrogen.

The invention is further illustrated by the following examples:

EXAMPLE 1

Figure 2:
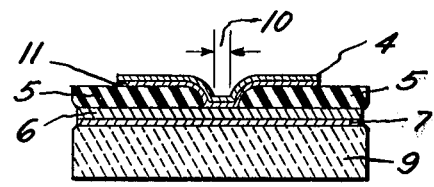
FIG. 2 is a cross sectional view of one of the detectors of FIG. 1 taken along the line 2—2.

A hydrogen detector was prepared having the construction shown in FIGS. 1 and 2.

Before use, the glass slide substrate was degreased and cleaned in a conventional manner. Specifically, the detector was made by successive depositions of thin films on a standard glass microscope slide, about 75 mm long and about 25 mm wide. The first film was a 1000 Å thick layer of Ti metal layer of sputter deposited onto the clean dry slide. This layer was covered by a sputter deposited 2000 Å film of $TiO_2$. The sputtering was done in an rf system in argon for Ti and in 50% argon, 50% $O_2$ for $TiO_2$. The pressure was approximately 2.5 Pa (18-20 microns) and the deposition rate was approximately 90 Å/min. X-ray diffraction showed the films to be principally anatase, with a trace of rutile.

The above films covered the entire slide except for two small areas of Ti metal left uncovered near the ends of the slide for contacts to that film.

A coating of lacquer (Hunt Waycoat negative photoresist) was painted by hand over the $TiO_2$ layer, except for a 2-3 mm strip down the center of the slide and the two Ti contact areas. After this coating was thoroughly dried and polymerized by exposure to uv light, a series of gold cross strips, 200 Å thick, 1 mm wide, and 18 mm long was evaporated, i.e. this vapor deposition was carried out in a conventional manner in a vacuum using an electron beam to evaporate gold from a crucible. In substantially the same manner, a series of platinum cross trips, 200 Å thick, 1 mm wide and 18 mm long was evaporated and vapor deposited on all the gold strips. Each platinum strip was substantially coextensive with a gold strip and was in electrical contact therewith. Each cross strip of platinum, where it comes in contact with the exposed $TiO_2$ layer constitutes one hydrogen detector. Thus a number of independent detectors were formed on each microscope slide.

The detector was tested by attaching leads to the Ti and Pt films with indium solder, after first applying contact pads of silver paint. A potentiostat (Pine Instruments Co. RDE 3) acted as a regulated power supply and current converter. For logarithmic current plots, a Kiethley Model 26000 Logarithmic Picoammeter in series with a resistor measured the output voltage of the potentiostat's current indicator. The platinum, gold and titanium films of the detector were electrically conducting, and the $TiO_2$ film sandwiched between the gold and titanium films was electrically insulating in the absence of hydrogen. In what follows, the voltage or bias is that of the Pt film with respect to the Ti film.

The detector slide was mounted inside a jar through which the test gas could be flowed and then vented to air.

The test gas was made by mixing hydrogen with air through a two-stage dilution system consisting of valves and flow meters. The mixed gas passed through a drying (Drierite) tube and a small 3-way valve mounted near the test chamber. This arrangement allowed the gas flow to be diverted to the room while it was adjusted to the desired mixture and, after the feed lines had equilibrated, the gas was directed to the test chamber. Hydrogen was mixed with air because it was found that the current decreased very slowly after hydrogen removal if oxygen was not present in the ambient gas.

To the extent possible, the flow rate through the test chamber was held at about 2.5 SCFH ($\approx 20$ cm$^3$/sec) as indicated by the flow meters. At this rate, the test chamber had a complete change of gas in about 12 sec. All of the measurements were made under dc or slow sweep conditions (100 mV/sec).

Figure 3:
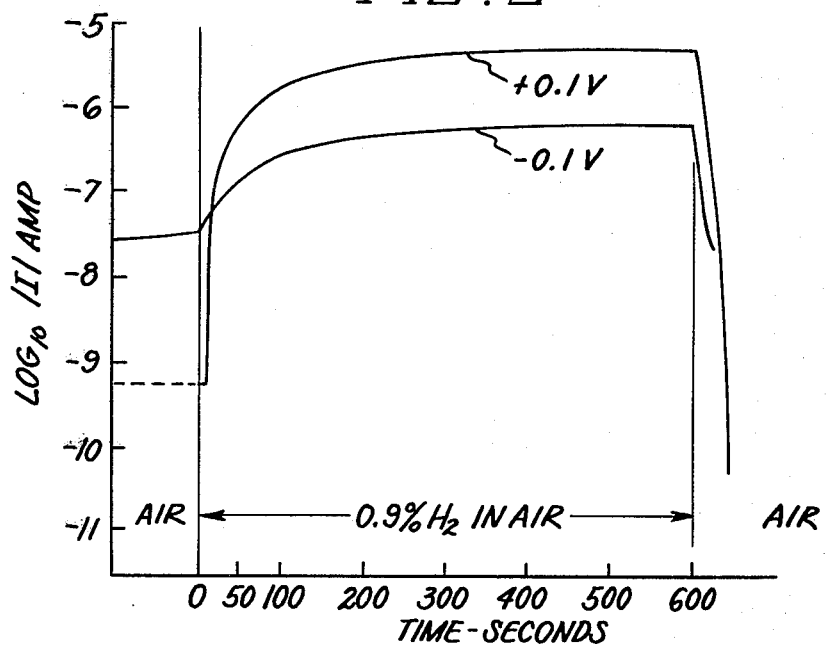
FIG. 3 shows the response and recovery of the present detector to 0.9% hydrogen in air at room temperature.

FIG. 3 shows the current response and recovery time for exposure of the detector to 0.9% of hydrogen in air at room temperature for a negative bias of 31 0.1 volt and a positive bias of +0.1 volt. FIG. 3 shows that the response when $H_2$ is introduced is quicker for positive bias than for negative, but the converse is true with respect to recovery.

FIG. 3 shows that saturation currents were reached within 10 minutes, and recovery occurred within about 1 minute after removal of $H_2$ from the ambient.

Figure 4:
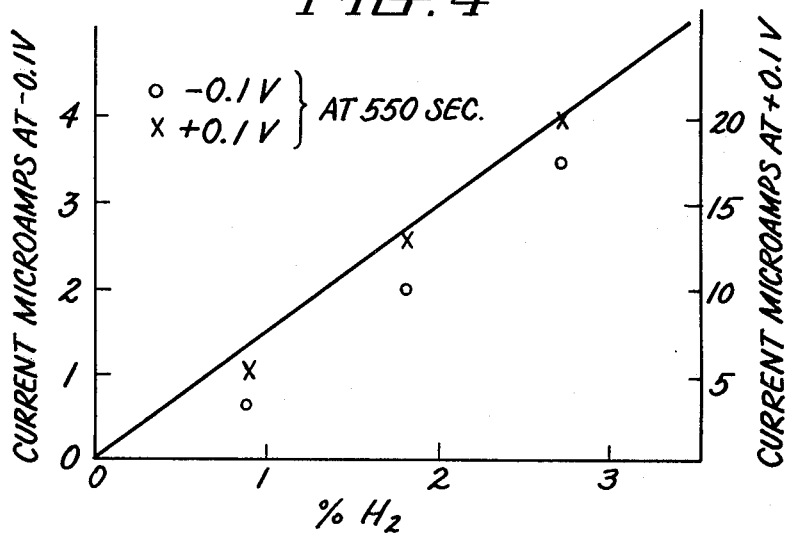
FIG. 4 shows the dependency of current on hydrogen concentration in air for the present detector with −0.1 volt as well as +0.1 volt applied at room temperature at 550 seconds after hydrogen is admitted to the atmosphere surrounding the detector.

FIG. 4 shows the dependence of current on $H_2$ concentration in air at 550 seconds at room temperature with $-0.1$ volt applied and also with $+0.1$ volt applied. As FIG. 4 shows, the response to $H_2$ concentrations from 0.9% to 3.6% in air was close to linear, and such linear response probably extends to even higher values, since a subsequent experiment with pure $H_2$ showed a much greater response.

EXAMPLE 2

A detector was prepared in the same manner as set forth in Example 1 except that the diffusion barrier film was elemental titanium. This detector was tested in substantially the same manner set forth in Example 1. The experiments showed that titanium as a diffusion barrier was unsuitable for practical use. This is because Ti does not form a Schottky barrier with $TiO_2$ so the base current is much higher.

EXAMPLE 3

In this example, the detector was the same as that set forth in Example 1. Also, the testing procedure was substantially the same as set forth in Example 1 except that the detector was tested in pure hydrogen at room temperature. Saturation current with both +0.1 volt and −0.1 volt applied was reached within about 10 minutes and recovery occurred within about 1 minute after removal of hydrogen from the ambient.

Saturation current was about 900 microamperes with +0.1 volt applied and about 200 microamperes with −0.1 volt applied.

What is claimed is:

1. A hydrogen detector comprised of a substrate supporting an electrically conducting base metal film, an upper electrically conducting diffusion barrier metal film, a polycrystalline film of titanium dioxide sandwiched between the base and diffusion barrier films, said polycrystalline titanium dioxide film electrically insulating the base film from said diffusion barrier film, the base film being in electrical contact with the titanium dioxide film, an insulating layer electrically insulating said titanium dioxide film from said diffusion barrier film except for a predetermined surface portion thereof in electrical contact with said diffusion barrier film, said predetermined electrically contacting portion being at least sufficiently large to produce a measurable electrical conductance, an electrically conducting or non-conducting catalytic top film of metal able to dissociate hydrogen into its atomic form in electrical contact with said diffusion barrier film and at least substantially coextensive with said barrier film throughout said predetermined electrically contacting portion, said top film when it is electrically conducting or said diffusion barrier film and said base film being electrically connected to an external circuit to measure conductance, the electrical conductance of said hydrogen detector varying with the concentration of hydrogen in the atmosphere surrounding it.

2. The hydrogen detector according to claim 1 wherein said base metal film is selected from the group consisting of titanium, gold, silver, nickel, tin, copper and alloys thereof.

3. The hydrogen detector according to claim 1 wherein said top metal film is selected from the group consisting of platinum, palladium and alloys thereof.

4. The hydrogen detector accorrding to claim 1 wherein said diffusion barrier film is a metal selected from the group consisting of gold, silver, nickel, indium, tin, copper and alloys thereof.

5. The hydrogen detector according to claim 1 wherein said top metal film is platinum, said diffusion barrier film is gold and said base metal film is titanium.

6. The hydrogen detector according to claim 1 wherein said top metal film is electrically non-conducting and said diffusion barrier film and said base film are connected to an external circuit to measure conductance.

7. The hydrogen detector according to claim 1 wherein said top metal film is electrically conducting and said top film and said base film are connected to an external circuit to measure conductance.

8. The hydrogen detector according to claim 1 wherein said top metal film is electrically conducting, and wherein said diffusion barrier and said base films are connected to an external circuit to measure conductance.

9. The hydrogen detector of claim 1 wherein said insulating layer is comprised of polymer.

10. The hydrogen detector of claim 1 wherein said insulating layer is comprised of silicon monoxide.

11. A hydrogen detector comprised of an electrically conducting metal substrate supporting a polycrystalline film of titanium dioxide, an upper electrically conducting diffusion barrier metal film, said polycrystalline film of titanium dioxide being sandwiched between the substrate and diffusion barrier film and electrically insulating the substrate from said diffusion barrier film, the substrate being in electrical contact with the titanium dioxide film, an insulating layer electrically insulating said titanium dioxide film from said diffusion barrier film except for a predetermined surface portion thereof in electrical contact with said diffusion barrier film, said predetermined electrically contacting portion being at least sufficiently large to produce a measurable electrical conductivity, an electrically conducting or non-conducting catalytic top film of metal able to dissociate hydrogen into atomic form in electrical contact with said diffusion barrier film and at least substantially coextensive with said barrier film throughout said predetermined electrically contacting portion, said top film when it is electrically conducting or said diffusion barrier film and said substrate being electrically connected to an external circuit to measure conductance, the electrical conductivity of said hydrogen detector varying with the concentration of hydrogen in the atmosphere surrounding it.

12. The hydrogen detector according to claim 11 wherein said substrate is selected from the group consisting of titanium, gold, silver, nickel, tin, copper and alloys thereof.

13. The hydrogen detector according to claim 11 wherein said top metal film is selected from the group consisting of platinum, palladium and alloys thereof.

14. The hydrogen detector according to claim 11 wherein said top metal film is platinum, said diffusion barrier film is gold and said substrate is titanium.

15. The hydrogen detector according to claim 11 wherein said top metal film is electrically non-conducting and said diffusion barrier film and said substrate are connected to an external circuit to measure conductance.

16. The hydrogen detector according to claim 11 wherein said top metal film is electrically conducting and said top film and said substrate are connected to an external circuit to measure conductance.

17. The hydrogen detector according to claim 11 wherein said top metal film is electrically conducting, and wherein said diffusion barrier film and said substrate are connected to an external circuit to measure conductance.

18. The hydrogen detector of claim 11 wherein said insulating layer is comprised of polymer.

19. The hydrogen detector of claim 11 wherein said insulating layer is comprised of silicon monoxide.

20. The hydrogen detector according to claim 11 wherein said diffusion barrier film is a metal selected from the group consisting of gold, silver, nickel, indium, tin, copper and alloys thereof.

* * * * *